United States Patent [19]

Swearingen et al.

[11] Patent Number: 4,559,110
[45] Date of Patent: Dec. 17, 1985

[54] ACETOPHENONE RECOVERY AND PURIFICATION

[75] Inventors: Loren L. Swearingen, Clute; Alfred W. Heinsohn, Freeport; Craig W. Snook, Lake Jackson; Wallace E. Embrey, Freeport; Garnet E. McConchie, Lake Jackson, all of Tex.

[73] Assignee: The Dow Chemical Company, Midland, Mich.

[21] Appl. No.: 512,508

[22] Filed: Jul. 11, 1983

[51] Int. Cl.[4] .............................................. B01D 3/10
[52] U.S. Cl. ..................................... 203/37; 203/17; 203/44; 203/45; 203/73; 203/80; 568/335; 568/749
[58] Field of Search ........................ 203/43, 44, 45, 37, 203/17, 74, 77, 73, 80; 568/324, 492, 749, 754, 313, 345, 390, 335

[56] References Cited

U.S. PATENT DOCUMENTS

| 2,597,497 | 5/1952 | Joris | 568/749 |
|---|---|---|---|
| 2,715,145 | 8/1955 | Bewley et al. | 568/324 |
| 2,727,074 | 12/1955 | Bewley | 203/36 |
| 2,824,048 | 2/1958 | Hupe et al. | 568/749 |
| 2,992,169 | 7/1961 | Gregory et al. | 203/36 |
| 3,668,256 | 6/1972 | Brundege | 203/37 |
| 4,169,109 | 9/1979 | Yoshida et al. | 568/313 |
| 4,283,568 | 8/1981 | Pujado | 568/754 |
| 4,298,765 | 11/1981 | Cochran et al. | 568/754 |

FOREIGN PATENT DOCUMENTS 0742496 12/1955 United Kingdom ................ 203/37

Primary Examiner—S. Leon Bashore
Assistant Examiner—V. Manoharan
Attorney, Agent, or Firm—A. C. Ancona

[57] ABSTRACT

Distillation of the heavy waste stream from the manufacture of phenol via the cumene process provides an overhead stream containing phenol, acetophenone and 2-phenyl propionaldehyde. Extraction of the overhead stream with aqueous caustic removes the phenol and subsequent distillation of the remaining two components in the presence of a catalytic amount of caustic provides a substantially pure acetophenone distillate.

10 Claims, 1 Drawing Figure

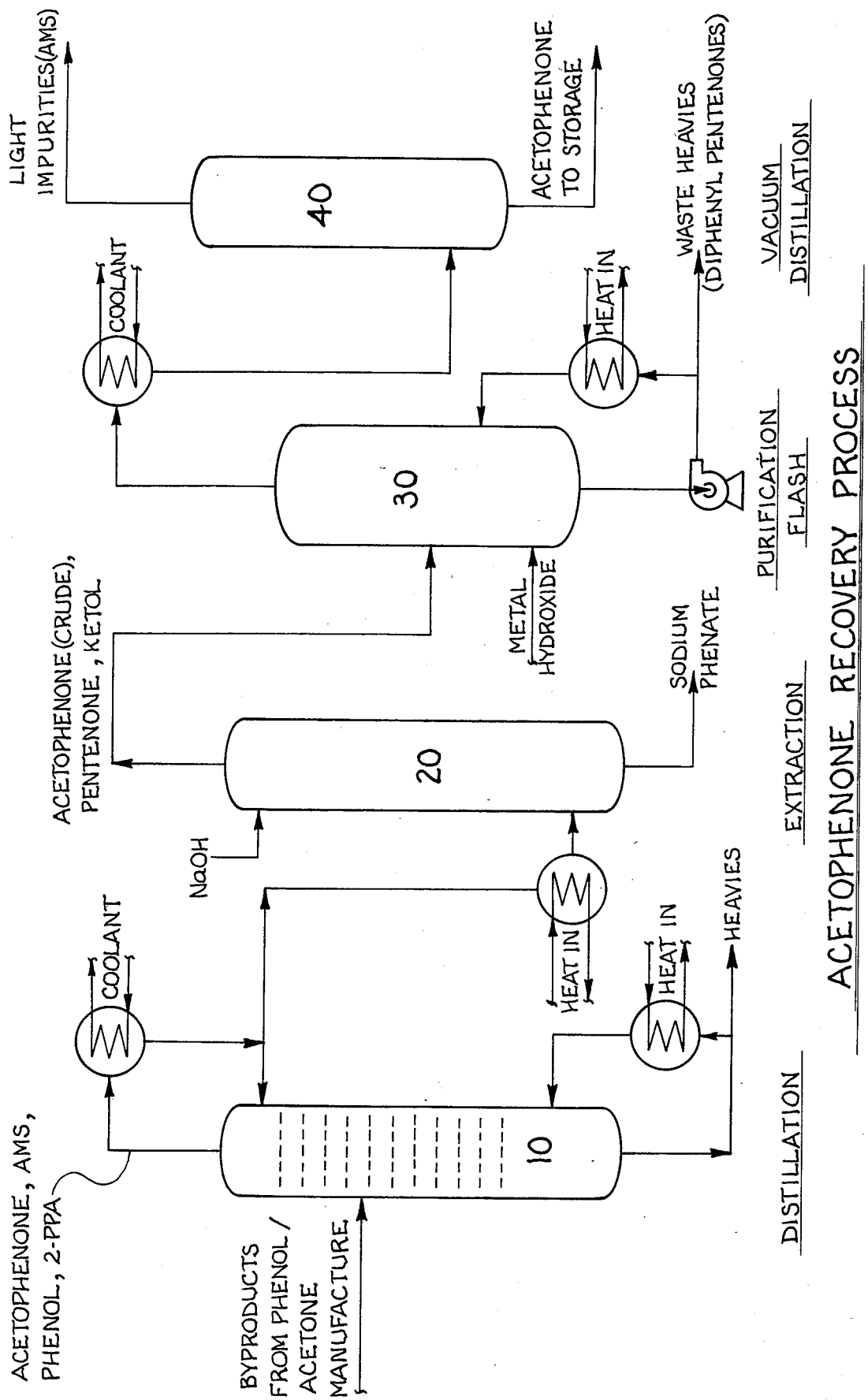

ACETOPHENONE RECOVERY AND PURIFICATION

BACKGROUND OF THE INVENTION

Manufacturing technology to produce phenol and acetone via the oxidation of cumene to cumene hydroperoxide and the subsequent decomposition of peroxide to phenol and acetone is well known and widely employed commercially. Numerous by-products, such as phenyl alcohols, aldehydes, and ketones, are also produced in the oxidation/decomposition process. One such by-product, acetophenone, is especially useful as an intermediate for the production of pharmaceuticals and specialty perfumes. Acetophenone also exhibits unique solvent properties useful in the manufacturing and processing of gums and resins.

Acetophenone from a phenol process is available only in the form of low purity product, generally less than 20%, and is contained in the plant waste heavies stream, which is typically burned for fuel value. Separation of the acetophenone and subsequent purification is extremely difficult due to the close proximity of its boiling point to azeotropes of other materials contained in the waste heavies, namely phenol and 2-phenyl propionaldehyde (2-PPA). Conventional distillation cannot be used to yield high purity acetophenone. The recovery of such products has been attempted in the past, but most such recovery processes are complex operations. Thus, in a process of separating acetophenone and 2-phenyl propionaldehyde (also called hydratropic aldehyde), the mixture is treated with an aqueous sodium bisulfite solution which with the latter forms a water soluble adduct. Acetophenone does not and, being insoluble in the aqueous solution, can be separated from it. This process is described in U.S. Pat. No. 3,379,768.

The present invention is directed toward a novel and improved method of separating acetophenone from a mixture thereof which contains phenol, 2-PPA, and phenolic heavies. Phenol can be separated from the other components by extraction with sodium hydroxide. The phenol in the form of sodium phenate, is soluble in the aqueous phase and can be later recovered as phenol using acid treatment. The remaining 2-PPA and acetophenone, having been separated from the aqueous phase, are catalytically reacted at high temperatures in the presence of caustic to form 1,4-diphenyl-3-hydroxy-1-pentanone and subsequently dehydrated to form 1,4-diphenyl-2-penten-1-one, 1,4-diphenyl-3-penten-1-one, and isomers thereof. The remaining acetophenone, being present in significantly larger amounts, can now be easily purified and separated from the heavy pentanones and pentenones by vacuum distillation.

SUMMARY OF THE INVENTION

The waste heavies from the manufacture of phenol and acetone, primarily phenyl alcohols, aldehydes, and ketones, are vacuum distilled to produce the crude acetophenone, 2-PPA, and phenol mixture. Phenol is removed via treatment with caustic to form sodium phenate and is recoverable from the aqueous stream via acid treatment. 2-PPA and acetophenone are reacted in the presence of caustic as a catalyst at high temperatures to form stable penten-1-one compounds, from which the acetophenone can be separated by distillation. Further distillation of the acetophenone to remove lights, primarily alpha methyl styrene, provides an extremely high purity acetophenone product.

DETAILED DESCRIPTION OF THE INVENTION

In the following description the distillation, flash and extraction columns are numbered and refer to the drawing.

In the manufacture of phenol via the cumene oxidation/decomposition process, once the phenol and acetone have been recovered, there remains a heavy by-products stream having the following approximate composition:

|  | Wt. % |
| --- | --- |
| Alpha methyl styrene | 0–1 |
| Phenol | 2–10 |
| Acetophenone | 5–25 |
| 2-Phenyl propionaldehyde | 0.7–3.5 |
| Heavy Phenolic and Diphenyl Compounds | 60–92 |

This heavies by-product stream is vacuum distilled in distillation column 10 at sub-ambient pressure ranging from 10 mm to 100 mm HgA and at temperatures ranging from 180° to 250° C. The column conditions minimize the unwanted thermal decomposition of phenolic heavies and allow for maximum acetophenone recovery in the distillate. The overhead product from distillation column 10 contains approximately:

|  | Wt. % |
| --- | --- |
| Alpha methyl styrene | 0–4 |
| Phenol | 10–40 |
| Acetophenone | 50–80 |
| 2-Phenyl propionaldehyde | 5–10 |
| Others | 0–5 |

The overall recovery of acetophenone via vacuum distillation is from 90 to 99.5%. The distillate is then treated in extraction column 20 with aqueous caustic containing from about 5 to 30% NaOH, but preferably 10 to 20% NaOH, by weight. The caustic facilitates the removal of phenol by generating the water soluble sodium phenate salt, which is removed at the bottom of extraction column 20 and also catalyzes a condensation reaction of 2-phenyl propionaldehyde with acetophenone. If solutions less than 5 weight % caustic are employed, phase separation problems are encountered between the organic and aqueous phases due to similar densities of the phases. If solutions greater than 33 weight % NaOH are used, the resulting sodium phenate product tends to precipitate out of the aqueous solution, thus causing difficulties in operation of the caustic extraction process. The mole ratio of NaOH to phenol is from about stoichiometric (with respect to the reaction to make sodium phenate) to 100% excess, but preferably 5–50% excess caustic. Other inorganic alkali and alkaline earth metal hydroxides may be employed, e.g. potassium, calcium and magnesium, in place of caustic.

Utilization of less than stoichiometric amounts of caustic results in poor phenol removal and the combining of organic and aqueous layers to yield one phase. Using an excess of more than 50% caustic is unnecessary, becomes uneconomical, and can also adversely affect extraction equipment operations. The overhead stream from distillation column 10 and aqueous caustic are contacted by any suitable means, e.g., a counter-current liquid-liquid extraction column 20 at a temperature of from about ambient to 200° C. but preferably 50° C. to 120° C. and at a pressure from about ambient to 500 psig but preferably from ambient to 200 psig. Column temperatures above 200° C. tend to promote the ketol self condensation of acetophenone while temperatures below 50° C. do not adequately dehydrate the pentanone heavies, which is necessary to stabilize the heavy during distillation. The ketol addition products, for example 1,4-diphenyl-3-hydroxy-pentan-1-one, exist in equilibrium with the original reactants (acetophenone and 2-PPA) and at elevated temperatures tend to thermally decompose to acetophenone, 2-PPA, and the corresponding aforementioned penten-1-ones. Time for contacting is usually from about 1 to about 180 minutes, but depends upon the efficiency of the contacting means. An extraction column operating at from 20 to 60 minutes contact time is sufficient to remove substantially all of the phenol and react essentially all of the 2-PPA at temperatures greater than 50° C. The aqueous phase exiting column 20 consists of about 5% to about 30% by weight sodium phenate plus residual unreacted sodium hydroxide. Residual organics in the aqueous phase are recycled to recover the phenol and other minor amounts of organics. The organic phase exiting the top of extraction column 20 contains approximately:

|  | Wt. % |
|---|---|
| Alpha methyl styrene | 0–5 |
| Phenol | 0–0.1 |
| Acetophenone | 70–90 |
| 2-PPA | 0–0.1 |
| 1,4-Diphenyl-2(or 3)-penten-1-one | 10–25 |
| Others | 0–2 |
| Water | 0.5–2.0 |

Water washing to remove any residual metal hydroxide is unnecessary since its presence at levels of 0.01 to 1.0 wt.% in the crude acetophenone will function as a catalyst for further condensation of unconverted 2-phenyl propionaldehyde with acetophenone in the final distillation step.

This crude acetophenone is then vacuum flashed in flash drum 30 at sub-ambient pressures ranging from 10 mm HgA to 100 mm HgA and temperatures of 120° to 200° C. to recover essentially all of the acetophenone in the overhead stream. The vacuum flash minimizes thermal decomposition of heavy compounds and minimizes side reactions. The overhead stream from flash drum 30 contains by weight approximately 90 to 99 wt.% acetophenone with no heavies present. The bottoms stream from flash drum 30 contains primarily the pentene-one heavies. The flashed overhead is saturated with water and contains up to 3 wt.% light components, primarily alpha methyl styrene. Vacuum distillation in column 40 at pressures ranging from 10 mm HgA to 100 mm HgA and temperatures ranging from 60° to 120° C. produces a purified acetophenone product containing from about 0.5 to 2.0% impurities by weight.

The following experiments are representative of the invention.

EXAMPLE 1

A 1.81 kg sample of phenolic heavies from a cumene oxidation/decomposition phenol process was distilled batchwise in a 20-tray Oldershaw glass column (1-inch diameter). The feed material contained:

| Component | Weight % |
|---|---|
| Alpha methyl styrene | <0.5 |
| Cumene | <0.01 |
| Phenol | 4.5 |
| 2-Phenyl propionaldehyde | 2.5 |
| Acetophenone | 11.0 |
| Heavy phenolics and diphenyl compounds | 81.5 |

The distillation column was operated at 20 mm HgA vacuum pressure with overhead (distillate) and bottom temperatures of up to 132° C. and 205° C., respectively. Analyses of the overhead and bottoms streams were made using conventional chromatography techniques. The results showed:

| Component/Weight % | Bottoms | Distillate |
|---|---|---|
| Alpha methyl styrene | 0.0 | 3.0 |
| Cumene | <0.01 | <0.01 |
| Phenol | 0.6 | 23.0 |
| 2-Phenyl propionaldehyde | 1.0 | 8.0 |
| Acetophenone | <0.1 | 63.0 |
| Heavy diphenyl compounds | 98.0 | 3.0 |
| Total weight, kg | 1.49 | 0.32 |

A 99+% recovery of acetophenone was achieved.

EXAMPLE 2

(A) A by-product heavies stream (4.29 kg) from a phenol process, similar to Example 1, was distilled at 100 mm HgA. The feed material contained:

| Component | Weight % |
|---|---|
| Alpha methyl styrene | <0.1 |
| Cumene | 1.1 |
| Phenol | 3.5 |
| 2-Phenyl propionaldehyde | 1.6 |
| Acetophenone | 12.3 |
| Heavy phenolics and diphenyl compounds | 81.4 |

The distillate and bottoms temperatures were 162° C. and 240° C., respectively.

(B) By-product heavies from a phenol process (1.13 kg) with a composition identical to that in (A) above were distilled at ambient pressure and overhead and bottoms temperatures of 205° C. and 313° C., respectively. The table below shows the distillate composition and acetophenone recovery for both (A) and (B) experiments.

| Distillate Composition, weight % | Example 2(A) | Example 2(B) |
|---|---|---|
| Alpha methyl styrene | 4.1 | 21.0 |
| Cumene | 0.2 | 16.2 |
| Phenol | 19.2 | 12.0 |
| 2-Phenyl propionaldehyde | 9.1 | 6.4 |
| Acetophenone | 58.5 | 38.1 |
| Heavy phenolics and diphenyl compounds | 8.9 | 6.3 |
| Acetophenone in Bottoms, % | 0.8 | 4.6 |
| Acetophenone Recovery | 92.9 | 79.0 |

Operation at a pressure of 100 mm HgA or greater favor unwanted thermal cracking of the heavies, reducing the overall acetophenone recovery purity.

EXAMPLE 3

A distillate material obtained using the same technique as in Example 1 was batchwise extracted with aqueous caustic in 8 consecutive extractions in 2-liter glass kettles. The extractions included 4 minutes mixing and 12 minutes settling times at 80° C. using a 0.72 weight ratio of caustic to organic feed. The caustic contained 15.0 weight % sodium hydroxide, representing an excess of 6% caustic based on stoichiometric phenol present. The organic feed and extracted product compositions are shown in the table below.

| Component, weight % | Feed | Product |
|---|---|---|
| Alpha methyl styrene | <1.0 | <0.5 |
| Cumene | <0.2 | 0.2 |
| Phenol | 24.0 | 0.3 |
| 2-Phenyl propionaldehyde | 11.0 | 3.2 |
| Acetophenone | 53.0 | 86.1 |
| Heavy phenolics and diphenyl compounds | 10.8 | 9.7 |
| % Phenol Removal | | 99.0 |
| % 2-Phenyl propionaldehyde removal | | 75.9 |
| % Acetophenone recovery | | 80.0 |
| Total Contact Time, min. | | 128.0 |

Only a minor amount (<1 wt.%) of acetophenone is soluble in the aqueous phase. The amount of acetophenone lost is accounted for by the reaction with and disappearance of 2-phenyl propionaldehyde.

EXAMPLE 4

Approximately 49.0 grams of the extraction product described in Example 3 was flashed (~1 theoretical tray) at atmospheric pressure in a 100 cc distillation flask equipped with heating mantle, water condenser, and thermometer for overheads and bottoms temperature measurement. The distillate was taken at an overhead temperature of 220° C., which corresponded to a bottoms temperature of 280° C. The organic feed and overhead product composition were:

| Component, weight % | Feed | Distillate |
|---|---|---|
| Alpha methyl styrene | <0.5 | <0.5 |
| Cumene | 0.2 | 1.1 |
| Phenol | 0.3 | 0.5 |
| 2-Phenyl propionaldehyde | 3.2 | <0.1 |
| Acetophenone | 86.1 | 95.1 |
| Heavy phenolic and diphenyl compounds | 9.7 | 2.7 |
| % Acetophenone Recovery | | 92.1% |
| % 2-Phenyl Propionaldehyde Removal | | 97.4% |

Cracking of heavy diphenyl and phenolic compounds led to the increased levels of cumene and phenol in the distillate.

EXAMPLE 5

A distillate feed material similar to that described in Example 3 was extracted with 16.5 wt.% aqueous sodium hydroxide using a continuous countercurrent extractor consisting of a 6.7-ft.×1.5-in. I.D. glass column packed with ¼-inch ceramic Intalox saddles. The extraction was carried out at ambient temperatures (23° C.) with 15.2 gm/min caustic introduced above the column packing and 11.4 gm/min organic feed introduced just below the column packing. The 1.33 weight ratio of caustic to organic feed represents an excess of 10% caustic based on stoichiometric phenol present. The organic feed and organic extraction product contained:

| Component, weight % | Feed | Product |
|---|---|---|
| Alpha methyl styrene | <0.1 | 0.4 |
| Cumene | <0.1 | <0.1 |
| Phenol | 47.1 | <0.1 |
| 2-Phenyl propionaldehyde | 7.5 | 6.3 |
| Acetophenone | 45.3 | 62.1 |
| Heavy phenolic and diphenyl compounds | <0.1 | 30.9 |
| Contact time | | 184 min. |
| % Phenol removal | | 99.9 |
| % 2-Phenyl propionaldehyde removal | | 56.5 |
| % Acetophenone recovered | | 60.4 |

EXAMPLE 6

A distillate material similar to that described in Example 3 was extracted using the identical continuous counter-current extractor described in Example 5. The organic and caustic (18% NaOH in $H_2O$) feed rates were 11.4 gm/min and 26.0 gm/min, respectively. This represents about a 75% excess caustic based on stoichiometric phenol present. The extraction was carried out at 80° C. and atmospheric pressure. The recovered extraction product was then vacuum flashed at 100 mm HgA using distillation equipment similar to that described in Example 4. The distillation was terminated at a 162° C. overhead temperature and a corresponding 200° C. bottoms temperature. Analyses of the organic feed to the extractor and the flashed overhead product are presented below:

| Component, weight % | Feed | Overhead Products |
|---|---|---|
| Alpha methyl styrene | 0.2 | 0.9 |
| Cumene | <0.1 | <0.1 |
| Phenol | 53.9 | <0.1 |
| 2-Phenyl propionaldehyde | 8.9 | 3.2 |
| Acetophenone | 35.7 | 94.0 |
| Heavy phenolic and diphenyl compounds | 1.2 | <1.7 |
| % Phenol removal | | 99.9 |
| % 2-Phenyl propionaldehyde removal | | 70.0 |

EXAMPLE 7

Approximately 1600 grams of a distillate material identical in composition with that described in Example 6 was batch-extracted with 18% aqueous sodium hydroxide at 110° C. The liquids were combined and heated to 110° C. for approximately ten minutes, then poured into a separatory funnel, shaken for two minutes, and allowed to phase separate. The organic phase was collected and re-extracted per the above procedure. 917 grams of the extraction product was vacuum flashed at 100 mm HgA using the equipment described in Example 4. The distillation was carried to a 200° C. overhead temperature which corresponds to a 250° C. bottoms temperature. The analyses of the flashed overhead product were as follows:

| Component, wt. % | Overhead Product |
|---|---|
| Alpha methyl styrene | 0.8 |
| Cumene | <0.1 |
| Phenol | <0.1 |
| 2-Phenyl propionaldehyde | <0.1 |
| Acetophenone | 95.7 |
| Heavy phenolic and diphenyl compounds | 3.3 |
| Contact time | ~25 minutes |

| Component, wt. % | Overhead Product |
| --- | --- |
| % Phenol removal | 99.9 |
| % 2-Phenyl propionaldehyde removal | 99.9 |

EXAMPLE 8

A distillate feed material similar to that described in Example 7 was batch extracted with 50% aqueous sodium hydroxide at 80° C. The batch extraction procedure was identical with that described in Example 7. The organic extracted product was water washed and vacuum distilled using a 20-tray Oldershaw column at 25 mm HgA and a reflux ratio of 1. Eleven separate distillate fractions were collected at overhead temperatures ranging from 25° C. to 100° C. The weight % analyses of the combined distillate fractions obtained at overhead temperatures of from 97° to 100° C. were:

| Component | Weight % |
| --- | --- |
| Alpha methyl styrene | <0.1 |
| Cumene | <0.01 |
| Phenol | <0.01 |
| 2-Phenyl propionaldehyde | <0.1 |
| Acetophenone | 99.0 |
| Heavy phenolic and diphenyl compounds | <0.1 |

The present invention, then, is a process for recovering acetophenone from a phenolic heavies waste stream, comprising the steps of:

A. Vacuum distillation using equipment designed to achieve an equivalent 5 to 30 theoretical plate efficiency at 5 to 100 mm HgA, and a bottoms temperature of from 125° to 250° C., for the removal of heavy phenolic and diphenyl compounds.

B. Extraction of distillate recovered in step "A" with aqueous metal hydroxides at temperatures from 25° C. to 200° C., pressures from 1 to 15 atmospheres and a contact time of from 20 to 200 minutes, for the removal of phenol and 2-phenyl propionaldehyde.

C. Vacuum distillation of organic extraction product recovered in step "B" using distillation equipment designed to achieve an equivalent 1 to 20 theoretical plate efficiencies at 5 to 100 mm HgA pressure and a bottoms temperature of from 100° C. to 250° C. for the removal of heavy condensation products generated in step "B".

We claim:

1. A process for recovering acetophenone from a phenolic heavies waste stream comprising the steps of (a) vacuum distilling said stream to recover overhead a distillate stream containing acetophenone, 2-phenyl propionaldehyde and phenol, (b) extracting said distillate stream with an aqueous solution of an alkali or alkaline earth metal hydroxide, having a concentration sufficient to provide an organic and an aqueous phase, to form sodium phenate and to substantially completely react 2-phenyl propionaldehyde with acetophenone to form a ketol addition product and at a temperature sufficient to dehydrate said addition product to form a diphenyl pentenone, (c) separating said aqueous phase which contains said phenol as sodium phenate from said organic phase, (d) distilling said organic phase in the presence of a catalytic amount of said metal hydroxide in order to dehydrate any remaining ketol addition product to form a diphenyl pentenone, (e) recovering said acetophenone overhead, leaving said pentenone as a bottoms product, and (f) further distilling said recovered acetophenone to remove lower boiling impurities to obtain a pure acetophenone.

2. The process of claim 1 wherein the bottoms temperature of the distillation in step (a) is less than about 250° C.

3. The process of claim 2 wherein the concentration of said aqueous metal hydroxide in said extraction solution in step (b) is at least 5% by weight.

4. Th process of claim 3 wherein the concentration is from about 10 to about 20% by weight.

5. The process of claim 3 wherein the extraction step (b) is carried out at a temperature of from about 80° to about 110° C.

6. The process of claim 4 wherein the mole ratio of metal hydroxide to phenol is at least 1.

7. The process of claim 6 wherein the contact time in step (b) is from about 40 to about 120 minutes.

8. The process of claim 7 wherein the metal hydroxide employed in steps (a) and (d) are the same.

9. The process of claim 8 wherein the metal hydroxide is an alkali metal hydroxide.

10. The process of claim 9 wherein the alkali metal hydroxide is sodium hydroxide.

* * * * *